United States Patent [19]

Waller et al.

[11] Patent Number: 5,596,146
[45] Date of Patent: Jan. 21, 1997

[54] PHOTOACOUSTIC MEASUREMENT OF UNBURNED CARBON IN FLY-ASH

[75] Inventors: David Waller, Ankeny; Robert C. Brown, Ames, both of Iowa

[73] Assignee: Iowa State University Research Foundation, Inc., Ames, Iowa

[21] Appl. No.: 254,153

[22] Filed: Jun. 6, 1994

[51] Int. Cl.⁶ .................................................. G01N 29/00
[52] U.S. Cl. .............................................. 73/590; 356/432
[58] Field of Search ................... 73/24.02, 590, 73/643; 356/432 T, 432; 250/341.6, 339.12, 341.1, 343

[56] References Cited

U.S. PATENT DOCUMENTS

| | | | |
|---|---|---|---|
| 3,938,365 | 2/1976 | Dewey, Jr. ................. | 73/24.02 |
| 3,948,345 | 4/1976 | Rosencwaig ............... | 73/659 |
| 4,028,932 | 6/1977 | Rosencwaig ............... | 73/579 |
| 4,129,385 | 12/1978 | Rosencwaig et al. ...... | 356/432 T |
| 4,622,845 | 11/1986 | Ryan et al. ................ | 73/24.02 |
| 4,817,413 | 4/1989 | Asano et al. .............. | 73/24.02 |
| 5,069,551 | 12/1991 | Brown ....................... | 356/432 |
| 5,075,552 | 12/1991 | McClelland et al. ...... | 250/341.1 |

OTHER PUBLICATIONS

Rosencwaig, Allan, "Photoacoustic Spectroscopy of Solids", Oct. 1977, pp. 337–343.
Rosencwaig, Photoacoustic Spectroscopy of Solids, Apr. 1973, pp. 305–308.
"Carbon-In-Ash Monitors", *Technology Review*, 1–14, a report prepared by the Electric Power Research Institute, Feb. 1994.
G. Diebold et al., "Observation of the optoacoustic effect in the microwave region", *Appl. Phys. Lett.*, 29, 447–449 (Oct. 1, 1976).
A. M. DiGioia, Jr., et al., "Reducing Power Generation Costs Via On-Line Meaurements and Reduction of Carbon in Fly Ash", presented at the Southeastern Electric Exchange Meeting, Bal Harbour, FL, Jun. 3, 1988.
J. Makansi, "Carbon-in flyash monitors shed new light on plant performance", *Power*, 43–45 (Dec. 1989).

*Primary Examiner*—Hezrone E. Williams
*Assistant Examiner*—Nashmiya Ashraf
*Attorney, Agent, or Firm*—Schwegman, Lundberg, Woessner & Kluth, P.A.

[57] ABSTRACT

The present invention provides a method and an apparatus for measuring the amount of unburned carbon in a sample of fly ash using infrared photoacoustic absorption. One preferred method according to the present invention involves directing modulated infrared radiation at a sample of fly ash and measuring the acoustic signal produced when the unburned carbon in the sample absorbs the radiation producing a thermal wave which propagates through the sample to generate a minute acoustic wave at interfaces between the carbon particles and gas surrounding the particles. One preferred apparatus includes a source of modulated infrared radiation, a chamber for containing the sample, a microphone to detect the acoustic signals, lock-in amplifier to separate the desired photoacoustic signal from noise at other frequencies, and a PC computer to provide output from the amplifier. This apparatus identifies the acoustic signal for determination of the amount of unburned carbon in the sample.

16 Claims, 6 Drawing Sheets

PHOTOACOUSTIC MEASUREMENT OF UNBURNED CARBON IN FLY-ASH

STATEMENT OF GOVERNMENT RIGHTS

This invention was made with government support under United States Department of Commerce Grant no. ITA 87-02. The United States Government has certain rights in the invention.

FIELD OF THE INVENTION

The present invention relates to the field of determining the amount of unburned carbon in a sample of fly ash. More particularly, the present invention provides a method and apparatus for determining the amount of unburned carbon in a sample of fly ash using photoacoustic absorption.

BACKGROUND OF THE INVENTION

The carbon content of fly ash is the major determinant of combustion efficiency for coal-fired boilers. Carbon content is presently measured offline by a Loss-On-Ignition (LOI) test. The LOI test is typically performed by collecting a sample of fly ash from the boiler, weighing the sample, heating the sample to a temperature sufficient to drive moisture from the sample, reweighing the sample to determine the moisture content in the sample when collected, reheating the sample in an air stream to a temperature sufficient to oxidize the carbon in the sample to carbon dioxide, and weighing the remaining sample to determine the carbon content by the difference in weight between the sample prior to oxidation of the carbon and after the oxidation step.

There are a number of disadvantages associated with the typical LOI test. One disadvantage is the tedious and time consuming steps necessary to treat the sample to provide the relevant dam. Furthermore, the LOI test may introduce inaccuracies into the data if mineral matte, such as limestone or other substances, are present which exhibit weight changes upon heating in addition to the changes caused by carbon oxidation.

SUMMARY OF THE INVENTION

The present invention provides a method and an apparatus for measuring the amount of unburned carbon in a sample of fly ash using infrared photoacoustic absorption.

One preferred method according to the present invention involves directing modulated infrared radiation at a sample of fly ash and measuring the acoustic signal produced when the unburned carbon in the sample absorbs the radiation producing a thermal wave which propagates through the sample to generate a minute acoustic wave at interfaces between the carbon particles and gas surrounding the particles. The acoustic signal is then measured and compared to known values which allow determination of the amount of unburned carbon in the sample.

One preferred apparatus includes a source of modulated infrared radiation, a chamber for containing the sample, a microphone to detect the acoustic signals and means for identifying the acoustic signal for determination of the amount of unburned carbon in the sample.

Advantages accorded by the present invention are the ability to quickly, inexpensively, accurately and reproducibly determine the amount of unburned particulate carbon in the fly ash on site, which is indicative of the efficiency of the coal-fired furnaces. The prompt, accurate measurement of unburned particulate carbon provides an opportunity to effectively control combustor efficiency and emissions of coal-fired furnaces. As described above, the LOI tests currently used are time-consuming, relatively expensive and difficult to conduct, with many chances for the introduction of error into the result.

Another advantage accorded by the present invention is its ability to be used with fly ash containing a variety of materials other than carbon as well as water without a significant effect on accuracy of the results.

These and other features and advantages according to the present invention will be apparent upon a reading of the detailed description contained below, along with reference to the drawings.

DETAILED DESCRIPTION OF THE INVENTION

The method and apparatus according to the present invention is based on detecting the acoustical signal generated when a bulk sample of fly ash absorbs modulated infrared radiation (the photoacoustic effect). This acoustic signal is detected by a sensitive microphone located in the photoacoustic cell which contains the fly ash sample. It is important to select an IR wavelength that is strongly absorbed by the carbon in the fly ash but is only weakly absorbed by mineral matter or water in the fly ash.

Figure 1:
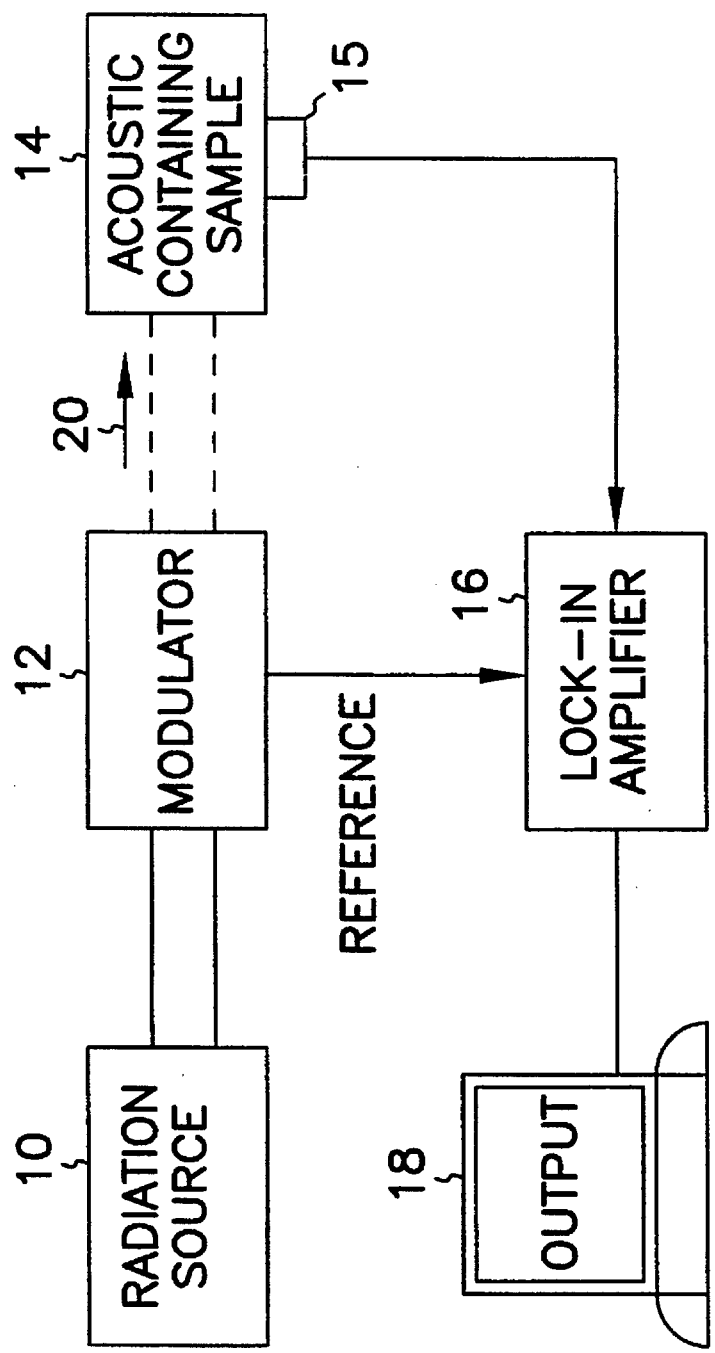
FIG. 1 is a schematic diagram of an apparatus according to the present invention.

One preferred apparatus according to the present invention is depicted schematically in FIG. 1. The apparatus includes a radiation source 10, modulator 12, photoacoustic cell 14 which contains the sample of fly ash, a sensitive microphone 15, lock-in amplifier 16, and a means for providing output 18 from the amplifier 16.

The radiation source 10 can be either a diode laser or light emitting diode (LED) operating in one of the wavelength ranges described above or a broadband (white) light source used in conjunction with an optical filter to select an appropriate wavelength band. Primarily, though, the source 10 must only have the ability to produce radiation in the desired wavebands.

Modulation of the radiation can be accomplished by a variety of techniques. If a dime laser is used as the radiation source 10, the modulator would typically comprise circuitry to electrically modulate the laser to produce an appropriate modulation frequency. If the radiation source 10 is a broadband source, modulator 12 would typically comprise an optical beam chopper. Other methods and apparatus for producing modulation of the radiation will be known to those skilled in the art.

The preferred photoacoustic cell 14 is an air-tight chamber machined from aluminum or brass that can be opened to admit a sample holder cup. A window at the top of the chamber admits a beam of radiation to the fly ash sample contained in the holder cup. The microphone 15 is mounted in the side of the chamber in close proximity to the holder cup to detect the photoacoustic signal generated in the fly ash.

In the preferred embodiment a preamplifier (not shown) is provided to strengthen the signal from the microphone 15 before it is processed by the lock-in amplifier 16. The lock-in amplifier 16, a commercially available component, discriminates against all signals but the one generated at the modulation frequency of radiation entering the photoacoustic cell. A PC computer is used as the preferred means for providing output 18 from the amplifier 16.

A representative fly ash sample is placed in the sample holder cup, which in the preferred embodiment holds about 5 g of fly ash. A spatula is slid across the sample to bring it level with the top edge of the holder cup. The holder cup is placed in the photoacoustic cell 14 and the cell is closed. The instrument is designed to analyze fly ash samples in an atmosphere of air but the cell could be evacuated and filled with a low molecular weight gas such as helium to increase detection sensitivity.

Figure 2:
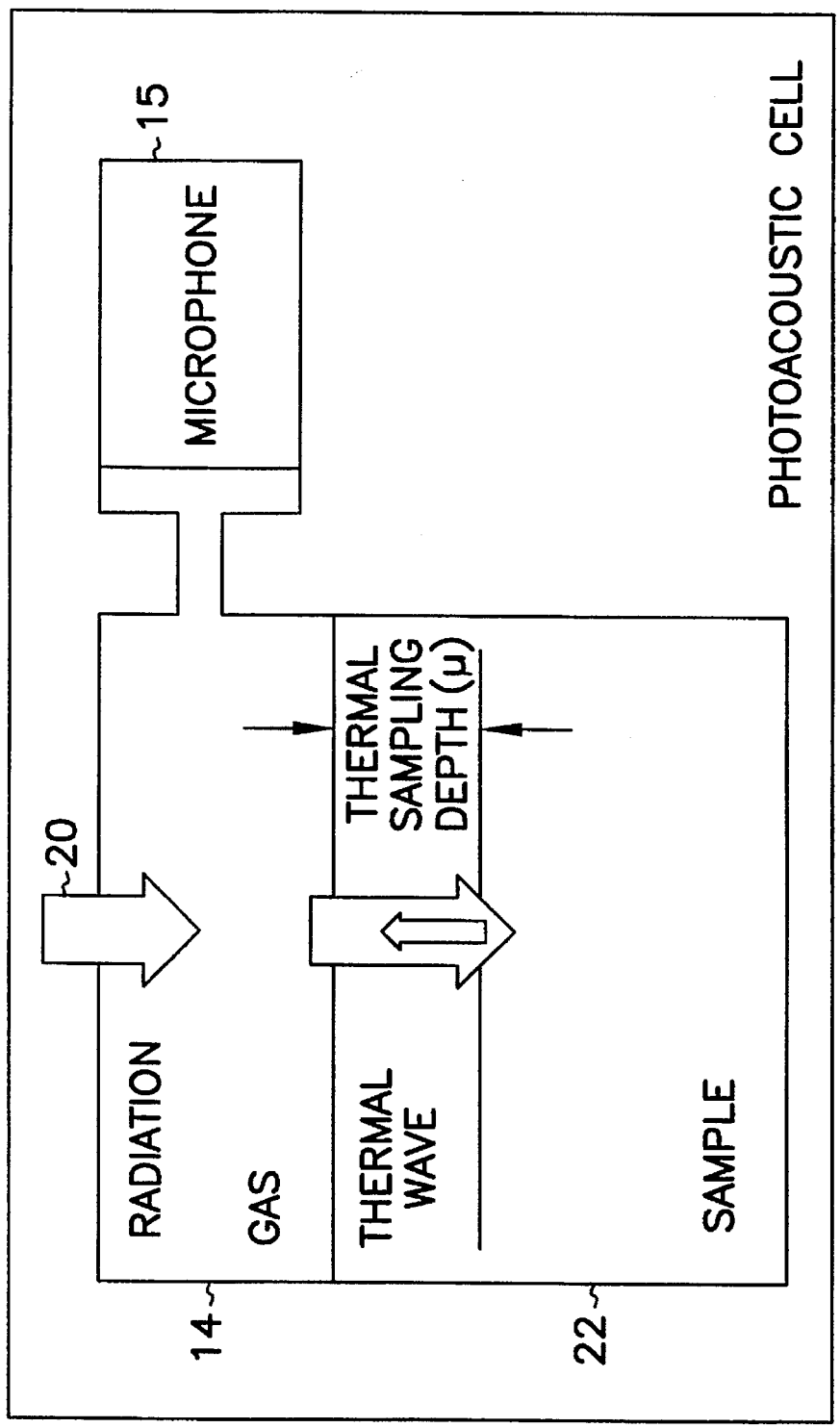
FIG. 2 is a schematic diagram of a photoacoustic chamber according to the present invention, depicting the absorption of radiation and propagation of a thermal wave within the sample.

Referring now to FIG. 2, which schematically depicts the process of generating the photoacoustic signal. As shown, a beam 20 of modulated IR radiation enters through a window at the top of the cell 14 and illuminates the sample of fly ash 22. Carbon particles in the fly ash 22 preferentially absorb the radiation and are heated. Because of the heating, a thermal wave propagates through the carbon particles to the particle-air interface where a minute acoustical signal is generated at a frequency equal to the modulation frequency of the radiation source. This acoustical signal is detected by the microphone 15 in the side of the photoacoustic cell 14. The microphone 15 generates a signal which is amplified in a preamplifier (not shown) and sent to the lock-in amplifier 16 which separates the desired photoacoustic signal from noise at other frequencies.

The preferred wavelengths for operation of the radiation source 10 are about 1.3 to about 1.55 μm and a second range of about 3.7 to about 3.8 μm. Experimental results indicate that the absorption of energy by materials other than the unburned carbon is minimized when these wavelength regions are used, which results in a photoacoustic signal providing an accurate indication of the amount of unburned carbon in the sample.

Modulation of the radiation source 10 may also be used to optimize the accuracy of the results achieved with the present invention. Higher modulation frequencies can delay the onset of saturation as more fully described below, which allows higher levels of carbon concentration to be measured before saturation. Increasing modulation frequency must, however, be balanced with decreases in signal strength to optimize the apparatus and method according to the present invention.

A modulation frequency of about 650 Hz is preferred for detection of up to about 5% weight of unburned carbon in fly ash from pulverized coal boilers. Higher modulation frequencies are preferred if higher concentrations of unburned carbon are to be detected because the use of higher frequencies delays the onset of saturation. Modulation frequencies below 650 Hz are preferred if the fly ash is expected to contain a significant number of carbon particles with diameters larger than about 75 μm. If higher modulation frequencies are desired but the samples typically contain larger carbon particles, grinding the samples before irradiation may increase accuracy by reducing the size of larger carbon particles which may not absorb energy as well as smaller carbon particles.

Another technique to delay the onset of saturation is to decrease the depth of the sample holder cup which, in turn, delays the onset of saturation by decreasing the thermal sampling depth which is more fully discussed below.

Yet another technique of delaying the onset saturation is dilution of the sample with an infrared-transparent material which is thoroughly mixed in with the sample.

The basis for the present invention lies in the preferential photoacoustic absorption of energy in selected wavebands by unburned carbon particles in fly ash. Photoacoustic absorption is the process of molecular absorption of modulated electromagnetic radiation leading to the production of an acoustic signal. In photoacoustic absorption, a sample contained in a closed, gas-filled chamber is illuminated with incoherent, amplitude-modulated radiation, which is absorbed at wavelengths corresponding to the sample's molecular vibrational frequencies. Through collisional deexcitation, this absorbed energy is quickly released into the surrounding gas as heat. The heated gas expands and creates a pressure, or acoustic wave at the modulation frequency of the absorbed radiation. This wave can be detected by a sensitive microphone, which produces the photoacoustic signal.

Photoacoustic theory of solids and condensed samples has been recently developed. With assumptions appropriate for a thermally thick, optically opaque solid sample in a closed, gas-filled cell, the photoacoustic signal magnitude, q, and phase φ, can be alternatively expressed as $$q = C \left( \frac{1}{\rho_s C_{p,s} k_s} \right)^{1/2} \left[ \frac{(\beta \mu_s)^2}{(\beta \mu_s + 1)^2 + 1} \right]^{1/2} \quad (1)$$

and $$\phi = \tan^{-1} \left( 1 + \frac{2}{\beta \mu_s} \right) \quad (2)$$

where $$C = I_o \gamma P_o \frac{k_g^{1/2}}{4 l_g T_o \pi f (\rho_g C_{p,g})^{1/2}} \quad (3)$$

and ρ is the density, $C_p$ is the specific heat, k is the thermal conductivity, β is the optical absorption (or decay) coefficient, μ is the thermal sampling depth, $I_o$ is the incident radiation intensity, γ is the ratio of specific heats, $P_o$ is the gas pressure, l is the length of the cell, $T_o$ is the gas temperature, and f is the modulation frequency of the radiation. The subscripts s and g denote sample and gas, respectively.

The product of βμ is very important to understanding photoacoustic signal behavior. At radiation wavelengths absorbed only by unburned carbon, β of the sample is proportional only to the carbon mass fraction. The thermal sampling depth, μ, in which the absorbed energy is released thermally to produce the photoacoustic signal, can be related to the thermal-wave decay coefficient, α, by $$\mu = \frac{1}{a} = \left(\frac{D}{\pi f}\right)^{1/2} \quad (4)$$

where D, the thermal conductivity, is given by:

$$D = \frac{k}{\rho C_p} \quad (5)$$

The values of $\rho$, $C_p$, and k for carbon particles in a bulk fly-ash sample can be assumed constant.

For the measurement of carbon in fly-ash, a signal directly proportional to the concentration of carbon is desired. When the product $\beta\mu<1$, the signal magnitude and phase given by Eqs. 1 and 2 are unsaturated, and are directly proportional to $\beta$, and hence, carbon concentration. Under unsaturated conditions, very little of the incident radiation is absorbed within a distance $\mu$ into the sample. Any increase in absorption causes a proportional increase in the thermal signal. However, as $\beta\mu$ approaches unity, the signal loses linearity in $\beta$, eventually becoming completely saturated as $\beta\mu$ approaches infinity. Physically, this represents the case where nearly all the radiation is absorbed within a distance $\mu$ into the sample and contributes thermally to the photoacoustic signal. Any increase in carbon concentration, $\beta$, beyond this point does not affect the photoacoustic signal significantly, and the signal becomes independent of carbon concentration or saturated. The phase of a saturated signal approaches $\pi/4$, also becoming independent of carbon concentration.

Inspection of Eqs. 1–5 provides some useful information regarding signal behavior and its dependence on both carbon particle size and modulation frequency. The size of absorbing carbon particles can affect the proportionality between the optical absorption coefficient, $\beta$, and the mass fraction, $m_c$, of the absorbing carbon particles. For example, the core of a spherical carbon particle of diameter larger than twice the thermal sampling depth $\mu$, when irradiated evenly over its entire surface, will not contribute to the photoacoustic signal, and remain "unheard". Grinding or other methods of controlling the size of the unburned carbon particles can be used to insure the proportionality of the photoacoustic signal to the concentration of the unburned carbon in the fly ash.

The dependence of the photoacoustic signal on modulation frequency can be seen from Eqs. 3 and 4 and their relationship in Eqs. 1, 2, and 6. The coefficient C and thermal sampling depth $\mu$ are proportional to $f^{-1}$ and $f^{-1/2}$, respectively. Consequently, an unsaturated ($\beta\mu<1$) signal varies as $f^{-3/2}$, while a saturated signal varies as $f^{-1}$. Increasing the modulation frequency will delay the onset of saturation by decreasing the value of $\mu$ allowing a greater carbon concentration to be measured before saturation. However, a tradeoff between signal strength and saturation onset is observed.

EXAMPLES

Following are examples obtained by experimental testing of fly ash samples using an apparatus and method falling within the scope of the present invention. The following examples are not to be construed as limiting the scope of the invention, which is defined by the claims.

1. Experimental Procedure

Fly-ash samples were obtained from one CFBC and seven PC boilers operated under varying conditions and with different coals. X-ray diffraction, thermogravimetric analysis (TGA), and microscopic investigation indicated that these samples contain different amounts of unburned carbon and a veracity of glasses and other compounds of widely varying particle sizes.

The carbon concentration of each sample was determined by a total organic carbon (TOG) test, performed by an independent laboratory. In this procedure, a few hundred milligrams of each sample were combusted completely in a Leco analyzer, converting all the carbon in the sample to $CO_2$, which was trapped and measured as total carbon, or TC. The same laboratory also performed an inorganic carbon (IC) test using a Coulometric analyzer, which washed the samples in an acid train to remove the carbonate carbon, which was also trapped and measured. The difference between the TC and IC tests represented the mass fraction of organic, unburned carbon, $m_c$.

The photoacoustic data was taken on a Perkin-Elmer 1800 FTIR coupled to a Perkin-Elmer 7500 computer. An MTEC Model 200 photoacoustic cell, powered by an MTEC power supply with adjustable gain (1, 2, 4, ..., 128) was used with the system. Microphone sensitivity was 50 mV/Pa, and the load cell volume was under 0.25 cm³. A commercially available spectrometer was used because it provided the desired radiation and it will be understood that the method according to the present invention could be practiced using any appropriate source of radiation and associated hardware necessary to carry out the method as described in the claims.

Each sample was hand-tumbled gently in its jar for five minutes prior to testing to ensure sample homogeneity. Each sample was then carefully spooned into a small aluminum sample cup approximately 0.2 cm³, and the surface was leveled with a small spatula so that the cup was uniformly filled for each test. The sample cup was placed in the sample holder over a small amount of magnesium perchlorate desiccant. The sample holder was then loaded into the photoacoustic cell, which was purged with ultra-highly purity helium at 10 cm³/sec. The power supply gain was set to maximize the interferrogram centerburst intensity without overloading the system. The optical path difference (OPD), or interferometer mirror velocity, was set at 0.25 cm/sec, corresponding to a modulation frequency of 650 Hz at a wavelength of about 3.85 µm.

2. Experimental Results

The organic carbon concentration of the fly-ash samples, ranging from 0.19% to 10.64%, agreed closely with those estimated by TGA and LOI methods. Uncertainty for the total carbon amounts ranged from 2% to 13%, while uncertainty for organic carbon ranged from 3% to 14%, based on a student-t statistical distribution using a 90% confidence level. This uncertainty is acceptable for our purposes, but may be reduced with further analysis.

Figure 3:
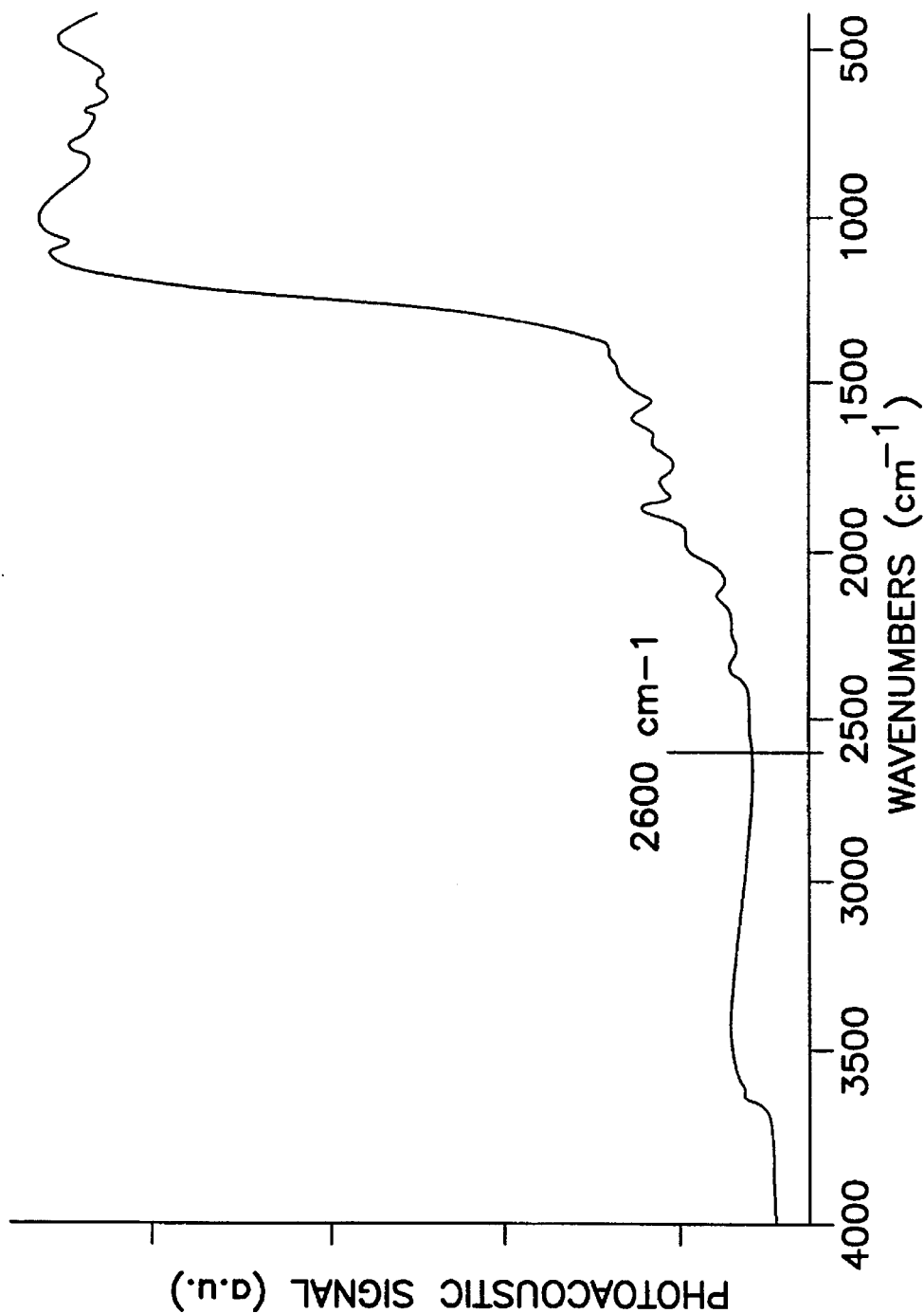
FIG. 3 is a graph depicting the relative intensity of photoacoustic signals generated over a range of wavenumbers from 4000 $cm^{-1}$ to 500 $cm^{-1}$ (wavelengths of 2.5 µm to 20 µm).

The photoacoustic signal magnitude at wavenumber 2602.6 cm$^{-1}$ was recorded from a spectral plot of photoacoustic absorbance vs. modulation frequency (from wavenumbers of 4000 cm$^{-1}$ to 500 cm$^{-1}$), an example of which is shown in FIG. 3. The lack of major spectral features around 2600 cm$^{-1}$ indicate the spectral value at this point is primarily based on organic, unburned carbon, although minor interference from water vapor or other compounds may be present. The signal was multiplied by the ratio 128/gain, where gain is that of the power supply, to reference all signals to the same scale.

The saturation value of the photoacoustic signal is $$q = C\left(\frac{1}{\rho_s C_{p,s} k_s}\right)^{1/2} \quad (6)$$

which is assumed to be approximately independent of the fly-ash sample. Hence, this value can be used to normalize photoacoustic dam and allow an accurate curve fit when the individual values of C, ρ, $C_{p,s}$, and $k_s$ are unknown.

Figure 4:
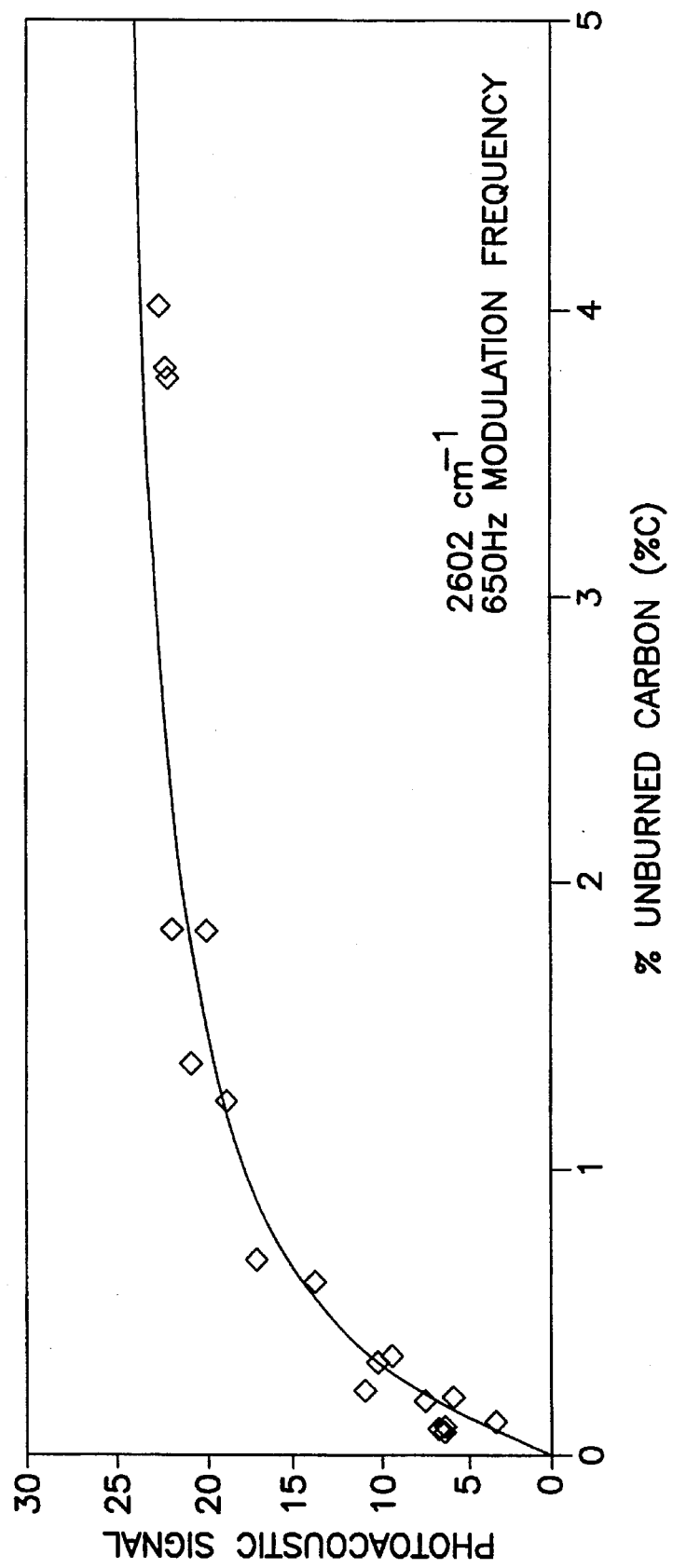
FIG. 4 is a graph depicting experimental results of tests conducted on samples with unburned carbon contents of up to 5%.
Figure 5:
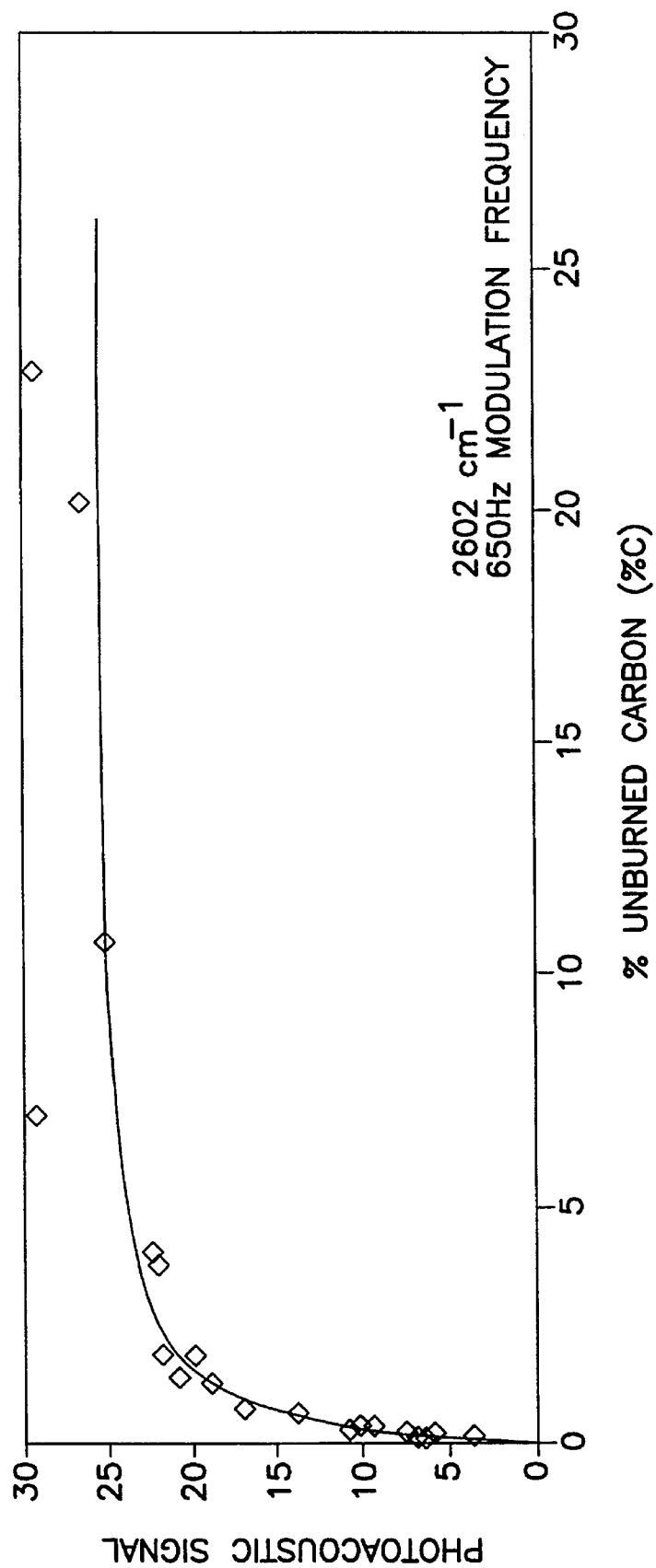
FIG. 5 is a graph depicting experimental results of tests conducted on samples with unburned carbon contents of up to about 25%.

This procedure was followed using an estimated asymptote for the normalized photoacoustic data plotted against organic carbon mass fraction in FIGS. 4 & 5. Acceptable photoacoustic uncertainties of 1% to 8% were determined using a student-t statistical distribution with a 90% confidence interval.

The theoretical curve of Eq. 1 (normalized, as mentioned above) was fit by trial and error to the experimental data by setting $$\beta\mu = 250\, m_c \quad (7)$$

and is also plotted in FIGS. 4 & 5. This experimentally determined relationship corresponds with the direct dependence of βμ on organic carbon concentration and the relatively constant value of μ for fly-ash samples (recall the values of $\pi_s$, $C_{p,s}$, and $k_s$ are assumed constant among the various types of fly-ash).

Excellent agreement between the experimental data and theoretical curve fit is observed, especially at the low organic carbon concentrations depicted in FIG. 4 which is typical of industrial fly-ash. At higher values of organic carbon, the match is still good, although in this range the experimental values are fairly sensitive to small changes in the normalization value. The agreement and relatively small error demonstrate the ability of photoacoustics to accurately and repeatable detect organic carbon in combustion fly-ash samples.

Figure 6:
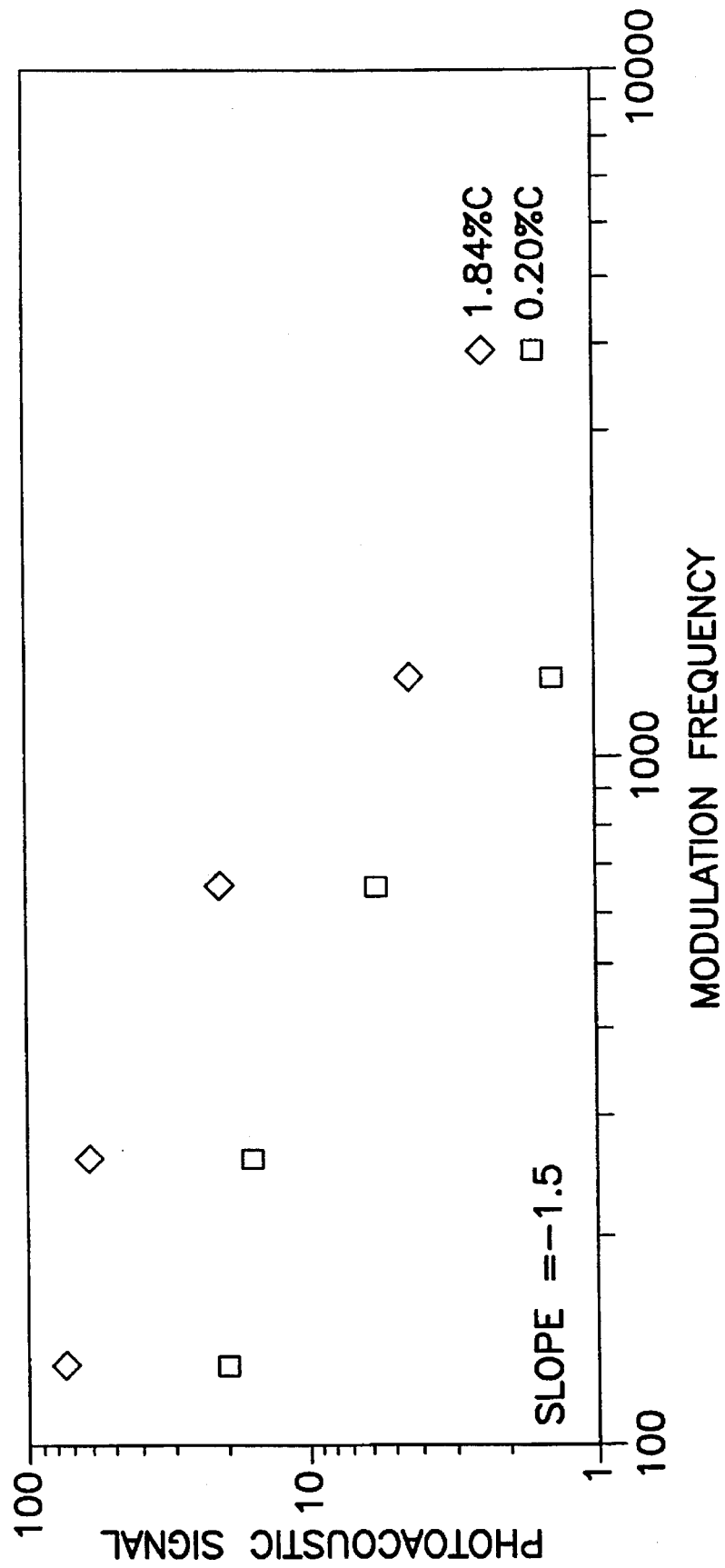
FIG. 6 is a graph depicting experimental results of photoacoustic signal strength as a function of modulation frequency for two samples of fly ash containing different amounts of unburned carbon particulates.

Two of the eight fly-ash samples ($m_c$ of 0.20% and 1.81%) were analyzed at a series of modulation frequencies (130 Hz, 260 Hz, 650 Hz, and 1300 Hz at a wavenumber of about 2600 $cm^{-1}$) to verify the theoretical photoacoustic signal dependence on modulation frequency of the electromagnetic radiation. A plot of the log of the unnormalized photoacoustic signal vs. the log of the modulation frequency is shown in FIG. 6, and similar behavior is noticed between the two curves.

A least squares linear fit among the three highest frequency points gives a slope of −1.5, which indicates unsaturated condition. However, between the lowest two frequencies, s a slope of −0.28 is observed, not −1, as expected by theory. This discrepancy can be explained by suggesting that the thermal sampling depth has been increased to near or beyond the IR absorption depth in the carbon particles. Decreasing the modulation frequency further results in little or no additional thermal contribution from the sample carbon, resulting in a disproportional small rise in photoacoustic signal magnitude. As a result, it would appear to be useful to maintain a modulation frequency of about 200 Hz or higher to limit the thermal sampling depth.

A more accurate fit between the theoretic curve and experimental data can be developed by evaluating a larger number of fly-ash samples and by using a more advanced curve-fitting techniques. Furthermore, increased accuracy may be obtained by choosing a modulation frequency which minimizes the effects of background noise and optimizes the absorption of energy by the unburned carbon particles.

Although specific methods and apparatus have been illustrated and described herein, it will be appreciated by those of ordinary skill in the art that any arrangement which is calculated to achieve the same purpose may be substituted for the specific methods and apparatus described. This application is intended to cover any adaptations or variations of the present invention. Therefore, it is manifestly intended that this invention be limited only by the claims and the equivalents thereof.

We claim:

1. A method of measuring the concentration of unburned carbon in a bulk sample of fly ash comprising the steps of:

a) holding the bulk sample stationary and directing modulated infrared radiation at the bulk sample, the infrared radiation having a wavelength in the range from about 3.7 to about 3.8 μm and a modulation frequency of about 200 Hz or above, wherein the modulated infrared radiation causes energy to be released from the sample within a certain depth from a surface of the sample called the thermal sampling depth;

b) controlling the modulated infrared radiation so that the product of an optical absorption coefficient for the sample and the thermal sampling depth is less than 1 to cause the acoustic signal to be substantially proportional to the concentration of unburned carbon in the sample; and c) detecting the acoustic signal produced by absorption of the infrared radiation, the acoustic signal being indicative of the concentration of unburned carbon in the sample.

2. A method of measuring the concentration of unburned carbon in a bulk sample of fly ash comprising the steps of:

a) holding the bulk sample stationary and directing modulated infrared radiation at the bulk sample; and b) detecting an acoustic signal produced by absorption of the infrared radiation by the unburned carbon in the bulk sample, the acoustic signal being indicative of the concentration of unburned carbon in the bulk sample, further wherein the modulated infrared radiation causes energy to be released from the sample within a certain depth from a surface of the sample called the thermal sampling depth and further comprising the step of controlling the modulated infrared radiation so that the product of an optical absorption coefficient for the sample and the thermal sampling depth is less than 1 to cause the acoustic signal to be substantially proportional to the concentration of unburned carbon in the sample.

3. A method according to claim 2, further comprising the step of placing the sample in a sample holder cup before the step of directing.

4. A method according to claim 2, wherein the step of directing further comprises infrared radiation having a wavelength in the range from about 3.7 to about 3.8 μm.

5. A method according to claim 2, wherein the step of directing further comprises infrared radiation having a wavelength in the range from about 1.3 to about 1.55 μm.

6. A method according to claim 2, wherein the step of directing further comprises modulating the infrared radiation at about 650 Hz.

7. A method according to claim 2, wherein the step of directing further comprises modulating the infrared radiation at about 650 Hz or below when the sample contains unburned carbon particles having a diameter of about 75 μm or above.

8. A method according to claim 2, wherein the step of directing further comprises modulating the infrared radiation at about 200 Hz or above.

9. A method according to claim 3, wherein the sample holder cup holds about 5 g of fly ash.

10. A method according to claim 2, further comprising the step of mixing a material transparent to infrared radiation in the sample.

11. A method according to claim 2, further comprising the step of grinding the sample before the step of directing.

12. A method of measuring the concentration of unburned carbon in a bulk sample of fly ash comprising the steps of:
   a) holding the bulk sample stationary and directing modulated infrared radiation at the bulk sample, the infrared radiation having a wavelength in the range from about 1.3 to about 1.55 µm and a modulation frequency of about 200 Hz or above, wherein the modulated infrared radiation causes energy to be released from the sample within a certain depth from a surface of the sample called the thermal sampling depth;
   b) controlling the modulated infrared radiation so that the product of an optical absorption coefficient for the sample and the thermal sampling depth is less than 1 to cause the acoustic signal to be substantially proportional to the concentration of unburned carbon in the sample; and
   c) detecting the acoustic signal produced by absorption of the infrared radiation, the acoustic signal being indicative of the concentration of unburned carbon in the sample.

13. A method according to claim 4 wherein the infrared radiation has a modulation frequency of about 200 Hz.

14. A method according to claim 4 wherein the infrared radiation has a modulation frequency of about 650 Hz.

15. A method according to claim 5 wherein the infrared radiation has a modulation frequency of about 200 Hz.

16. A method according to claim 5 wherein the infrared radiation has a modulation frequency of about 650 Hz.

* * * * *